(12) United States Patent
Omoto et al.

(10) Patent No.: US 10,096,766 B2
(45) Date of Patent: Oct. 9, 2018

(54) METHOD FOR EVALUATING PIEZOELECTRIC FILM, PIEZOELECTRIC ELEMENT, LIQUID EJECTING HEAD, AND LIQUID EJECTING APPARATUS

(71) Applicant: SEIKO EPSON CORPORATION, Tokyo (JP)

(72) Inventors: Masayuki Omoto, Chino (JP); Toshiki Hara, Suwa (JP); Ichiro Asaoka, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/812,816

(22) Filed: Nov. 14, 2017

(65) Prior Publication Data

US 2018/0145246 A1    May 24, 2018

(30) Foreign Application Priority Data

Nov. 22, 2016    (JP) ................................. 2016-226672

(51) Int. Cl.
    *B41J 2/14*          (2006.01)
    *H01L 41/187*     (2006.01)
    *G01N 23/085*    (2018.01)

(52) U.S. Cl.
    CPC ...... *H01L 41/1876* (2013.01); *B41J 2/14233* (2013.01); *G01N 23/085* (2018.02);
    (Continued)

(58) Field of Classification Search
    CPC .... B41J 2/14233; B41J 2202/03; B41J 2/161; B41J 2002/14241; B41J 2/14201;
    (Continued)

(56) References Cited

U.S. PATENT DOCUMENTS 8,177,995 B2 *   5/2012   Kobayashi ............... B41J 2/161
                                                                   239/102.2
8,215,753 B2 *   7/2012   Arakawa ............... C04B 35/493
                                                                     347/68
(Continued)

FOREIGN PATENT DOCUMENTS

JP      2001-223404      8/2001
JP      2008-094707      4/2008
(Continued)

OTHER PUBLICATIONS

Malic, "EXAFS Study of Thermal Treatment of Pb—Zr Alkoxide Precursors". Journal de Physique IV Colloque, 1997, 7 (C2), pp. C2-1193-C2-1194.
(Continued)

*Primary Examiner* — Jannelle M Lebron
(74) *Attorney, Agent, or Firm* — Workman Nydegger

(57) ABSTRACT

A method for evaluating a piezoelectric film containing a perovskite oxide containing a lead atom, a zirconium atom, and a titanium atom, and the method includes a process of irradiating the piezoelectric film with X-rays to acquire an extended X-ray absorption fine structure (EXAFS) spectrum at the L3 absorption edge of the lead atom, a process of Fourier-transforming the extended X-ray absorption fine structure (EXAFS) spectrum to acquire a radial distribution function, and a process of acquiring the intensity of a first peak having a distance from the lead atom of 1.4±0.2 Å, the intensity of a second peak having a distance from the lead atom of 2.0±0.2 Å, and the intensity of a third peak having a distance from the lead atom of 2.6±0.2 Å from the radial distribution function, and then evaluating the film quality of the piezoelectric film from a value obtained by dividing the intensity of the first peak by the intensity of the second peak
(Continued)

and a value obtained by dividing the intensity of the first peak by the intensity of the third peak.

4 Claims, 5 Drawing Sheets

(52) U.S. Cl.
CPC ............ *B41J 2002/14241* (2013.01); *B41J 2002/14419* (2013.01); *B41J 2202/03* (2013.01); *G01N 2223/041* (2013.01); *G01N 2223/61* (2013.01)

(58) Field of Classification Search
CPC ........ B41J 2002/14419; H01L 41/0973; H01L 41/1876; H01L 41/18; H01L 41/0805; H01L 41/187; H01L 41/1875; G01N 2223/041; G01N 2223/61; G01N 23/085
USPC ..... 347/20, 68, 70, 71; 252/62.9 PZ, 62.9 R; 310/311, 358, 393
See application file for complete search history.

(56) References Cited

U.S. PATENT DOCUMENTS

| | | |
|---|---|---|
| 2008/0074471 A1 | 3/2008 | Sakashita et al. |
| 2010/0253749 A1 | 10/2010 | Arakawa et al. |
| 2011/0216132 A1 | 9/2011 | Sakashita et al. |
| 2016/0064646 A1 | 3/2016 | Kawada et al. |

FOREIGN PATENT DOCUMENTS

| | | |
|---|---|---|
| JP | 2010-182783 | 8/2010 |
| WO | 2014-185379 | 11/2014 |

OTHER PUBLICATIONS

Arcon, "EXAFS study of PZT sols". Material Research Bulletin 38 (2003) 1901-1906 EXAFS study of PZT sols.

* cited by examiner

METHOD FOR EVALUATING PIEZOELECTRIC FILM, PIEZOELECTRIC ELEMENT, LIQUID EJECTING HEAD, AND LIQUID EJECTING APPARATUS

BACKGROUND

1. Technical Field

The present invention relates to a method for evaluating a piezoelectric film, a piezoelectric element having a piezoelectric film optimized by the evaluation method, a liquid ejecting head having the piezoelectric element, and a liquid ejecting apparatus having the liquid ejecting head.

2. Related Art

Among perovskite oxides represented by General Formula $ABO_3$, lead zirconate titanate in which a lead atom is disposed at the A-site and a zirconium atom and a titanium atom are disposed at the B-site has excellent piezoelectric characteristics, and therefore has been used for a piezoelectric film of a liquid ejecting head of an ink jet recording apparatus (liquid ejecting apparatus) (for example, JP-A-2001-223404).

In the liquid ejecting apparatus described in JP-A-2001-223404, the piezoelectric film is formed by a sol-gel method. In detail, the piezoelectric film is formed by firing a gel film which is a precursor of the piezoelectric film. However, when the gel film is fired, the lead atom evaporates, which degrades the piezoelectric characteristics of the piezoelectric film. Therefore, the lead atoms have been excessively blended in the piezoelectric film and the optimal excessive ratio (amount of the lead atoms to be excessively blended) of the lead atoms has been set according to the field intensity applied to a piezoelectric element.

Even in the case where the lead atoms are excessively blended in the piezoelectric film and the optimal excessive ratio of the lead atoms is set according to the field intensity applied to a piezoelectric element, the performance of the piezoelectric film may change depending on the states of the lead atoms disposed in the crystal lattice. For example, when the piezoelectric film has a portion (crystal defect) where no lead atom is disposed in the A-site, the crystal defect may cause an increase in a leakage current of the piezoelectric film and a reduction in a withstand voltage of the piezoelectric film. For example, when the lead atoms to be excessively blended in the piezoelectric film are disposed in the B-site in addition to the A-site, the piezoelectric characteristics of the piezoelectric film may deteriorate.

Therefore, in order to properly optimize the film quality of the piezoelectric film, in addition to setting the optimal excessive ratio of the lead atoms according to the field intensity applied to a piezoelectric element, it is necessary to grasp (evaluate) the states of the lead atoms disposed in the crystal lattice of the piezoelectric film. However, there has been a problem that there is no method for properly evaluating the states of the lead atoms disposed in the crystal lattice of the piezoelectric film, and thus it has been difficult to properly optimize the film quality of the piezoelectric film.

SUMMARY

The invention has been made in order to at least partially solve the above-described problem and can be realized as the following aspects or application examples.

Application Example 1

A method for evaluating a piezoelectric film according to this application example is a method for evaluating a piezoelectric film containing a perovskite oxide containing a lead atom, a zirconium atom, and a titanium atom, and the method includes a process of irradiating the piezoelectric film with X-rays to acquire an extended X-ray absorption fine structure (EXAFS) spectrum at the L3 absorption edge of the lead atom, a process of Fourier-transforming the extended X-ray absorption fine structure (EXAFS) spectrum to acquire a radial distribution function, and a process of acquiring the intensity of a first peak having a distance from the lead atom of 1.4±0.2 Å, the intensity of a second peak having a distance from the lead atom of 2.0±0.2 Å, and the intensity of a third peak having a distance from the lead atom of 2.6±0.2 Å from the radial distribution function, and then evaluating the film quality of the piezoelectric film from a value obtained by dividing the intensity of the first peak by the intensity of the second peak and a value obtained by dividing the intensity of the first peak by the intensity of the third peak.

The radial distribution function acquired by Fourier-transforming the extended X-ray absorption fine structure (EXAFS) spectrum at the L3 absorption edge of the lead atom has the first peak having a distance from the lead atom of 1.4±0.2 Å, the second peak having a distance from the lead atom of 2.0±0.2 Å, and the third peak having a distance from the lead atom of 2.6±0.2 Å.

The second peak having a distance from the lead atom of 2.0±0.2 Å and the third peak having a distance from the lead atom of 2.6±0.2 Å are peaks due to an oxygen atom disposed near the lead atom in the perfect crystal free from crystal defects and the like. In detail, the second peak is a peak due to an oxygen atom (closest oxygen atom) disposed closest to the lead atom and the third peak is a peak due to an oxygen atom (second closest oxygen atom) disposed second closest to the lead atom after the closest oxygen atom.

On the other hand, the first peak having a distance from the lead atom of 1.4±0.2 Å is a peak due to an oxygen atom disposed closest to the lead atom relative to the closest oxygen atom of the perfect crystal in a portion where the crystal is distorted. The portion where the crystal is distorted is a portion where the crystal has a crystal defect and the like and arises when the lead atom is not disposed in the original place (A-site), for example. Therefore, the degree of the distortion of the crystal changes depending on the state (level where the lead atom is not disposed in the original position) of the lead atoms disposed in the crystal lattice of the piezoelectric film and the intensity of the first peak changes. Accordingly, the state where the crystal is distorted, i.e., the states of the lead atoms disposed in the crystal lattice of the piezoelectric film, can be evaluated by evaluating the level (High or Low) of the intensity of the first peak.

In other words, in the radial distribution function obtained by Fourier-transforming the extended X-ray absorption fine structure (EXAFS) spectrum at the L3 absorption edge of the lead atom, when focusing on a specific peak (first peak) of the radial distribution function, the states of the lead atoms in the piezoelectric film can be evaluated in terms of the crystal level.

Since the first peak is information on the portion where the distortion is generated in the crystal, the intensity of the peak changes depending on the degree of the distortion of the crystal. Since the second peak and the third peak are information on portions where no distortion is generated in the crystal, the intensity of the peaks is less likely to change depending on the degree of the distortion of the crystal.

When only the intensity of the first peak is observed, in the case where the first peak has an abnormal value due to a disturbance, it may become difficult to properly evaluate the level (High or Low) of the intensity of the first peak due to the abnormal value. Therefore, it is preferable to grasp the intensity of the first peak by relative values (value obtained by dividing the intensity of the first peak by the intensity of the second peak, value obtained by dividing the intensity of the first peak by the intensity of the third peak) in which the second peak and the third peak, the intensities of the peaks of which are less likely to change depending on the degree of the distortion of the crystal, are reference values, and then evaluate the level (High or Low) of the intensity of the first peak by the relative values.

Furthermore, a case where the second peak and the third peak also have abnormal values due to a disturbance is assumed. Therefore it is preferable to evaluate the level (High or Low) of the intensity of the first peak by at least one of the relative value of the first peak in which the second peak is the reference value (value obtained by dividing the intensity of the first peak by the intensity of the second peak) and the relative value (value obtained by dividing the intensity of the first peak by the intensity of the third peak) of the first peak in which the third peak is the reference value.

Application Example 2

A piezoelectric element according to this application example is a piezoelectric element having a piezoelectric film containing a perovskite oxide containing a lead atom, a zirconium atom, and a titanium atom, in which a radial distribution function obtained by Fourier-transforming an extended X-ray absorption fine structure (EXAFS) spectrum at the L3 absorption edge of the lead atom of the piezoelectric film has a first peak having a distance from the lead atom of 1.4±0.2 Å, a second peak having a distance from the lead atom of 2.0±0.2 Å, and a third peak having a distance from the lead atom of 2.6±0.2 Å, and, when a value obtained by dividing the intensity of the first peak by the intensity of the second peak is defined as A and a value obtained by dividing the intensity of the first peak by the intensity of the third peak is defined as B, the piezoelectric film satisfies at least one of the conditions that the A is in the range of 0.35 to 0.75 and the B is in the range of 0.35 to 0.75.

The states of the lead atoms in the piezoelectric film can be evaluated in terms of the crystal level by the evaluation method described in the application example 1, and therefore the film quality of the piezoelectric film in the piezoelectric element can be optimized when the evaluation method described in the application example 1 is used.

Therefore, a piezoelectric film of the conditions derived by the evaluation method described in the application example 1 is preferable. More specifically, a piezoelectric film is preferable which satisfies at least one of the conditions that, when a value obtained by dividing the intensity of the first peak by the intensity of the second peak is defined as A and the intensity of the first peak is divided by the intensity of the third peak is defined as B, the A is in the range of 0.35 to 0.75 and the B is in the range of 0.35 to 0.75.

Furthermore, the film quality of the piezoelectric film is optimized, and therefore the piezoelectric element having the piezoelectric film has excellent performance.

Application Example 3

A liquid ejecting head according to this application example is a liquid ejecting head having a nozzle opening, a pressure generating chamber brought into communication with the nozzle opening, and a piezoelectric element and ejecting liquid from the nozzle opening by an operation of the piezoelectric element, in which the piezoelectric element has a piezoelectric film containing a perovskite oxide containing a lead atom, a zirconium atom, and a titanium atom, a radial distribution function obtained by Fourier-transforming an extended X-ray absorption fine structure (EXAFS) spectrum at the L3 absorption edge of the lead atom of the piezoelectric film has a first peak having a distance from the lead atom of 1.4±0.2 Å, a second peak having a distance from the lead atom of 2.0±0.2 Å, and a third peak having a distance from the lead atom of 2.6±0.2 Å, and, when a value obtained by dividing the intensity of the first peak by the intensity of the second peak is defined as A and a value obtained by dividing the intensity of the first peak by the intensity of the third peak is defined as B, the piezoelectric film satisfies at least one of the conditions that the A is in the range of 0.35 to 0.75 and the B is in the range of 0.35 to 0.75.

The state of the lead atom in the piezoelectric film can be evaluated in terms of the crystal level by the evaluation method described in the application example 1, and therefore the film quality of the piezoelectric film in the piezoelectric element of the liquid ejecting head can be optimized when the evaluation method described in the application example 1 is used.

Therefore, a piezoelectric film of the condition derived by the evaluation method described in the application example 1 is preferable. More specifically, a piezoelectric film is preferable which satisfies at least one of the conditions that, when a value obtained by dividing the intensity of the first peak by the intensity of the second peak is defined as A and the intensity of the first peak is divided by the intensity of the third peak is defined as B, the A is in the range of 0.35 to 0.75 and the B is in the range of 0.35 to 0.75.

Furthermore, the film quality of the piezoelectric film is optimized, and therefore a piezoelectric element having the piezoelectric film has excellent performance and a liquid ejecting head having the piezoelectric element also has excellent performance.

Application Example 4

A liquid ejecting apparatus according to this application example has the liquid ejecting head described in the application example above.

The film quality of the piezoelectric film is optimized by the evaluation method described in the application example 1, and therefore the piezoelectric element having the piezoelectric film has excellent performance and a liquid ejecting head having the piezoelectric element also has excellent performance. Furthermore, a liquid ejecting apparatus having the liquid ejecting head also has excellent characteristics.

BRIEF DESCRIPTION OF THE DRAWINGS

The invention will be described with reference to the accompanying drawings, wherein like numbers reference like elements.

DESCRIPTION OF EXEMPLARY EMBODIMENT

Hereinafter, an embodiment of the invention is described with reference to the drawings. This embodiment merely describes one aspect of the invention and does not limit the invention and can be arbitrarily altered within the range of the technical idea of an embodiment of the invention. In the following figures, the scales of layers or members are differentiated from the actual scales thereof so that the layers or the members are recognizable on the drawings.

Embodiment

Outline of Liquid Ejecting Apparatus

Figure 1:
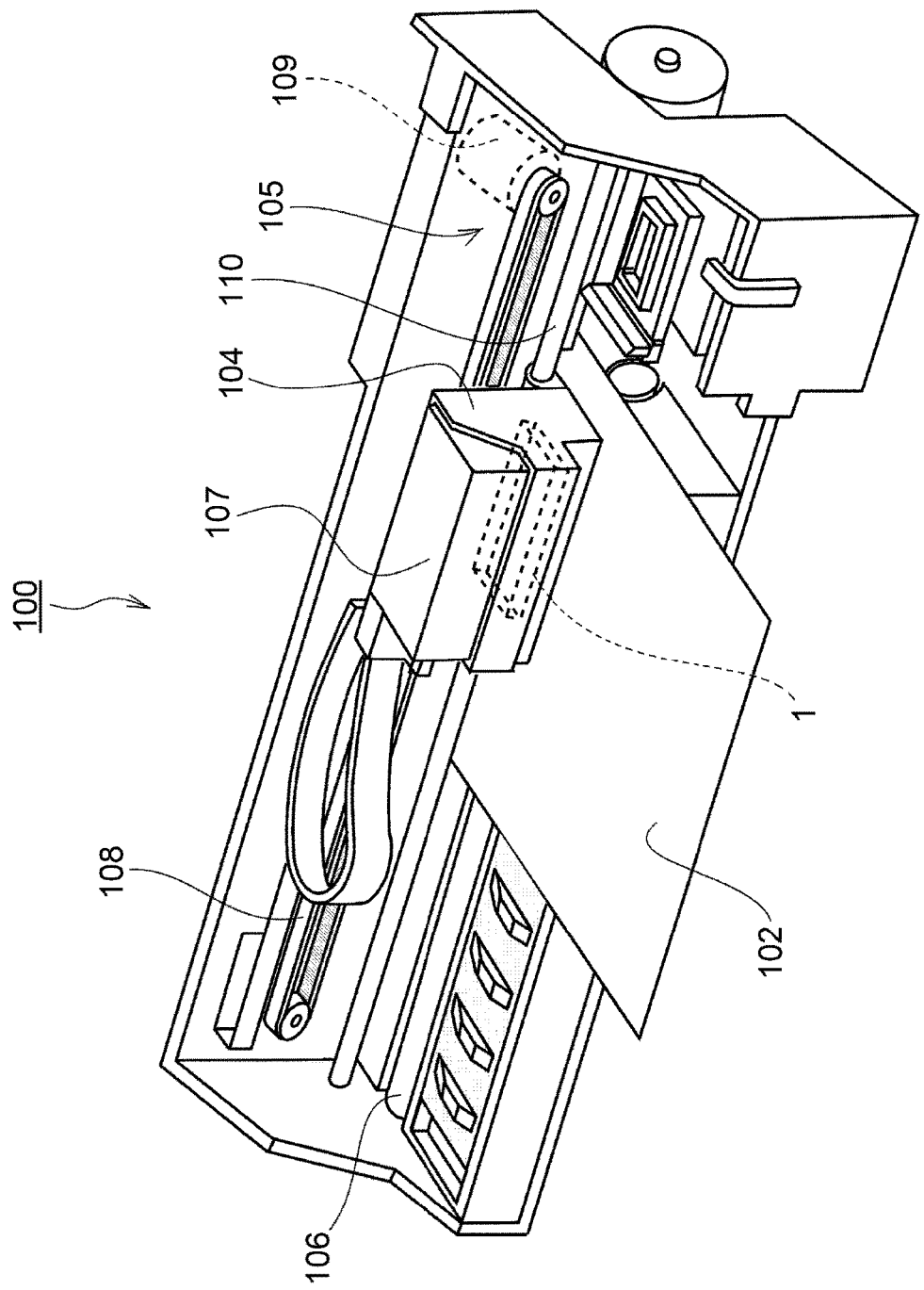
FIG. 1 is a perspective view illustrating the configuration of a liquid ejecting apparatus according to an embodiment.

FIG. 1 is a perspective view illustrating the configuration of a liquid ejecting apparatus according to an embodiment.

First, the outline of a liquid ejecting apparatus 100 in which a liquid ejecting head 1 is mounted is described with reference to FIG. 1.

As illustrated in FIG. 1, the liquid ejecting apparatus 100 is an ink jet printer ejecting an ink, which is an example of a "liquid", to print (record) an image and the like on a recording medium 102, such as a recording paper, and has a liquid ejecting head 1 ejecting the ink to the recording medium 102.

Furthermore, the liquid ejecting apparatus 100 has a carriage 104 to which the liquid ejecting head 1 is attached, a carriage moving mechanism 105 moving the carriage 104 in a main scanning direction (width direction of the recording medium 102), a transportation mechanism 106 transporting the recording medium 102 in a subscanning direction (direction crossing the main scanning direction), and the like. An ink cartridge 107 is detachably attached to the liquid ejecting head 1 and stores an ink.

The carriage moving mechanism 105 has a timing belt 108. The timing belt 108 is driven by a pulse motor 109, such as a DC motor. More specifically, when the pulse motor 109 operates, the liquid ejecting head 1 attached to the carriage 104 is guided by a guide rod 110 to move back and forth in the main scanning direction.

In the liquid ejecting apparatus 100, an operation of discharging an ink while moving the liquid ejecting head 1 in the main scanning direction and an operation of transporting the recording medium 102 in the subscanning direction are alternately repeated, whereby a desired image is printed on the recording medium 102.

Outline of Liquid Ejecting Head

Figure 2:
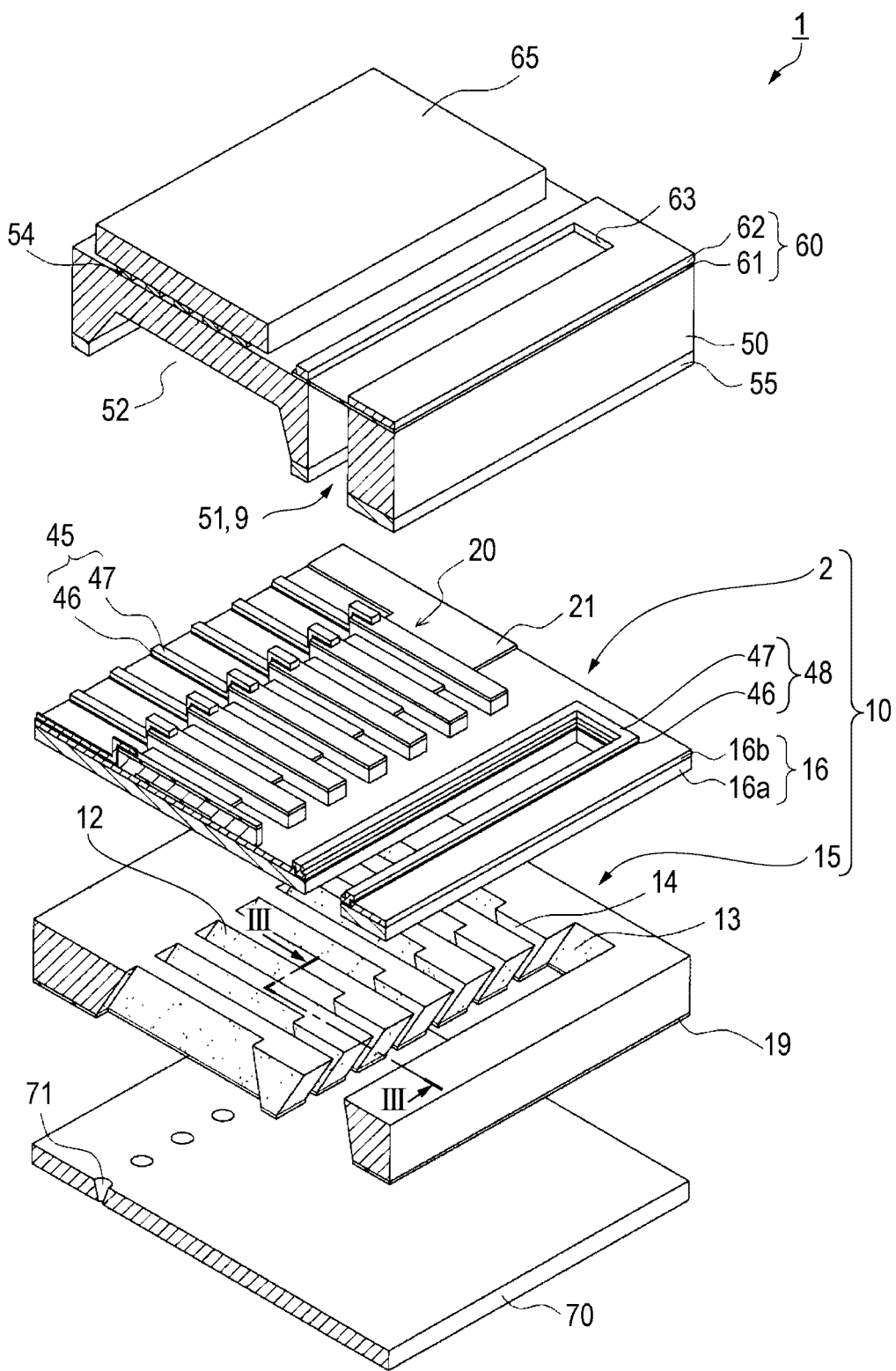
FIG. 2 is an exploded perspective view illustrating the configuration of a liquid ejecting head according to an embodiment.
Figure 3:
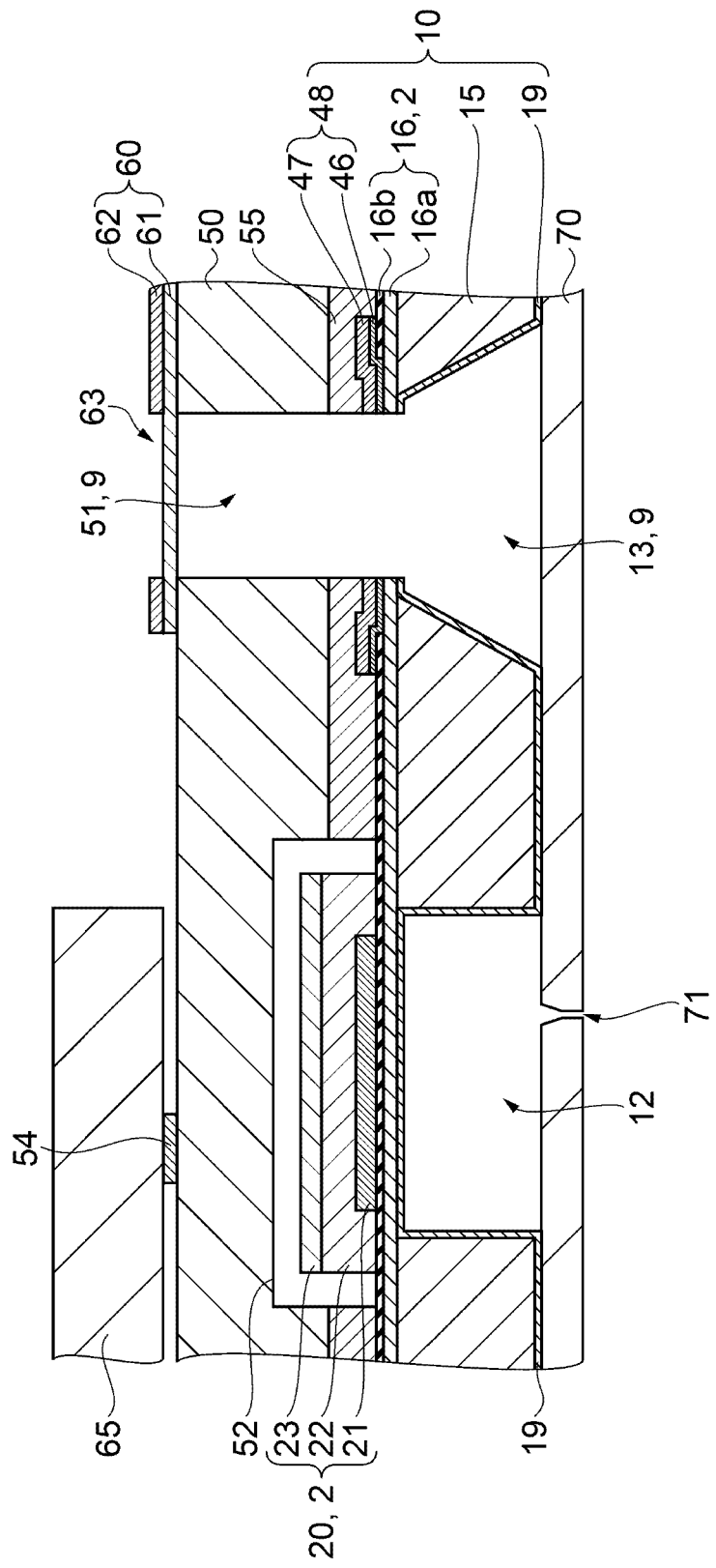
FIG. 3 is a schematic cross sectional view of the liquid ejecting head along the III-III line of FIG. 2.

FIG. 2 is an exploded perspective view illustrating the configuration of the liquid ejecting head 1 according to this embodiment. FIG. 3 is a schematic cross sectional view of the liquid ejecting head 1 along the III-III line of FIG. 2.

Next, the outline of the liquid ejecting head 1 is described with reference to FIG. 2 and FIG. 3.

As illustrated in FIG. 2 and FIG. 3, the liquid ejecting head 1 has a structure where a nozzle plate 70, a flow passage formation substrate 10 in which piezoelectric elements 20 are provided, a reservoir formation substrate 50, a compliance substrate 60, and a drive IC 65 are laminated in order.

The nozzle plate 70 is a substrate in which a nozzle opening 71 ejecting (discharging) an ink is formed and contains glass ceramics, a silicon substrate, stainless steel, or the like. The nozzle plate 70 is joined to the flow passage formation substrate 10 (base material 15) through an adhesive or a thermal fusion bonding film. Two or more of the nozzle openings 71 are arranged in one direction.

The flow passage formation substrate 10 has a base material 15 provided with pressure generating chambers 12, a communication portion 13, and ink supply ports 14, a protective film 19 covering the inner surface of the pressure generating chambers 12, the ink supply ports 14, and the communication portion 13, a pressure generating means 2 disposed on the surface opposite to the surface covered with the protective film 19 of the base material 15, lead electrodes 45 supplying a signal to the piezoelectric elements 20 of the pressure generating means 2, and a sealing layer 48 provided so as to surround the communication portion 13.

The base material 15 is a silicon substrate (silicon single crystal substrate) having the plane orientation <110>, for example. In the base material 15, the pressure generating chambers 12, the communication portion 13, and the ink supply ports 14 are formed by anisotropic etching using a potassium hydroxide (KOH) aqueous solution, for example.

The pressure generating chamber 12 is space which is long in a direction crossing the arrangement direction of the nozzle openings 71. Two or more of the pressure generating chambers 12 are arranged along the arrangement direction of the nozzle openings 71. The pressure generating chambers 12 are provided corresponding to the plurality of nozzle openings 71 in one-to-one relationship and are brought into communication with the nozzle openings 71. The communication portion 13 is space which is long in the arrangement direction of the nozzle openings 71 and is brought into communication with the pressure generating chambers 12 through the ink supply ports 14. The communication portion 13 configures a part of a reservoir 9 (common liquid chamber) brought into communication with the plurality of pressure generating chambers 12.

The pressure generating chambers 12, the ink supply ports 14, and the communication portion 13 are flow passages through which an ink flows and each thereof is space where an ink is stored. The ink is alkaline in many cases and an alkaline ink corrodes a silicon substrate. Therefore, the inner surfaces of the pressure generating chambers 12, the ink supply ports 14, and the communication portion 13 are covered with the protective film 19 to be protected.

The protective film 19 contains an ink-resistant material (alkali resistant material) which is hard to be corroded by the ink. Such a material is preferably tantalum oxide ($TaO_x$), such as tantalum pentoxide ($Ta_2O_5$).

The pressure generating means 2 is a thin plate-like device functioning as an actuator causing pressure fluctuation in an ink in each of the pressure generating chambers 12. The pressure generating means 2 contains a diaphragm 16 and the piezoelectric elements 20 giving pressure changes for causing the pressure generating chambers 12 to eject an ink.

The diaphragm 16 contains an elastic film 16a containing silicon oxide disposed on the surface opposite to the surface covered with the protective film 19 of the base material 15 and an insulating film 16b containing zirconium oxide laminated on the elastic film 16a. Moreover, the diaphragm 16 is provided with an opening at the position corresponding to the communication portion 13.

The piezoelectric element 20 is formed at a portion corresponding to the pressure generating chamber 12 of the diaphragm 16 (insulating film 16b). More specifically, the piezoelectric elements 20 arranged along the arrangement direction of the nozzle openings 71 are formed corresponding to the pressure generating chambers 12 arranged along the arrangement direction of the nozzle openings 71.

The piezoelectric element 20 has a configuration in which a lower electrode 21, a piezoelectric film 22, and an upper electrode 23 are laminated in this order from the insulating film 16b side. A portion containing the lower electrode 21, the piezoelectric film 22, and the upper electrode 23 is the piezoelectric element 20.

In general, one electrode of the lower electrode 21 and the upper electrode 23 is used as a common electrode and the other electrode of the lower electrode 21 and the upper electrode 23 and the piezoelectric film 22 are patterned for each of the pressure generating chambers 12, whereby the piezoelectric element 20 is formed. In this embodiment, the lower electrode 21 is used as the common electrode of the piezoelectric elements 20 and the upper electrode 23 is used as an individual electrode of the piezoelectric elements 20 but may be vice-versa on account of a drive circuit or wiring.

For the upper electrode 23 and the lower electrode 21, various metals, such as iridium, platinum, titanium, tungsten, tantalum, and molybdenum, alloys thereof, and the like are usable. The details of the piezoelectric film 22 are described later.

In order to supply a drive signal (drive pulse) to the piezoelectric elements 20, the lead electrode 45 is provided which is electrically connected to each of the upper electrodes 23 which are individual electrodes. Furthermore, on the diaphragm 16 (insulating film 16b) near the reservoir 9, the sealing layer 48 formed with the same material as that of the lead electrode 45 is provided. The lead electrode 45 and the sealing layer 48 contain an adhesion layer 46 disposed on the surface opposite to the surface covered with the protective film 19 of the base material 15 and a main metal layer 47 laminated on the adhesion layer 46. The adhesion layer 46 contains a nickel-chromium alloy. The main metal layer 47 contains gold.

Onto the surface on the side where the piezoelectric elements 20 are disposed of the flow passage formation substrate 10, the reservoir formation substrate 50 is joined through an adhesive 55. For the reservoir formation substrate 50, a silicon substrate, glass, a ceramics material, metal, resin, and the like are usable, for example.

The reservoir formation substrate 50 has a recessed portion (piezoelectric element holding portion 52) capable of accommodating the piezoelectric elements 20 and an empty portion (communication hole 51) penetrating the reservoir formation substrate 50. When the reservoir formation substrate 50 is joined to the flow passage formation substrate 10, the piezoelectric elements 20 are accommodated inside the piezoelectric element holding portion 52 and the reservoir 9 (common liquid chamber) is formed by the communication hole 51 and the communication portion 13. A region where the piezoelectric elements 20 are disposed is sealed by the adhesive 55 and the reservoir formation substrate 50 so as to be prevented from the entrance of moisture. As a result, degradation of the piezoelectric elements 20 due to the entrance of moisture is prevented.

To the surface opposite to the flow passage formation substrate 10 of the reservoir formation substrate 50, the compliance-substrate 60 and the drive IC 65 are joined.

The compliance substrate 60 contains the sealing film 61 and a fixed plate 62. The sealing film 61 is a polyphenylene sulfide (PPS) film having a thickness of about 4 to 8 μm, for example. The sealing film 61 contains a material having low rigidity and having flexibility and seals one surface of the communication hole 51. The fixed plate 62 is stainless steel (SUS) having a thickness of about 20 to 40 μm, for example, and hard materials, such as metal, are usable. The fixed plate 62 is provided with an opening 63 in a region facing the reservoir 9.

The drive IC 65 is connected to connection wiring 54 formed on the reservoir formation substrate 50 and electrically connected to the lead electrodes 45 through drive wiring (not illustrated). The drive IC 65 supplies a signal driving (operating) the piezoelectric elements 20.

Due to such a configuration, an ink from the ink cartridge 107 is supplied to the pressure generating chambers 12 through the reservoir 9 and the ink supply ports 14 in the liquid ejecting head 1. In the state where the ink is supplied to the pressure generating chambers 12, a drive signal of the drive IC 65 is supplied to the piezoelectric elements 20 through the lead electrodes 45 to operate the piezoelectric elements 20 to cause pressure fluctuation in the pressure generating chambers 12. By utilizing the pressure fluctuation, the liquid ejecting head 1 can eject the ink from the nozzle openings 71.

More specifically, the liquid ejecting head 1 has a configuration of having the nozzle openings 71, the pressure generating chambers 12 brought into communication with the nozzle openings 71, and the piezoelectric elements 20 and ejecting an ink from the nozzle openings 71 by the operation of the piezoelectric elements 20.

Formation Method and Problem of Piezoelectric Film

Next, a formation method and a problem of the piezoelectric film 22 are described.

The piezoelectric film 22 is metal oxide (perovskite oxide) having a perovskite structure represented by General Formula $ABO_3$, in which a lead atom is disposed in the A-site and a zirconium atom and a titanium atom is disposed in the B-site. More specifically, the piezoelectric film 22 is lead zirconate titanate (PZT) and is a perovskite oxide containing a lead atom, a zirconium atom, and a titanium atom.

In the following description, the atom (lead atom) disposed in the A-site is referred to as an A-site atom and the atom (zirconium atom, titanium atom) disposed in the B-site is referred to as a B-site atom in the perovskite oxide represented by General Formula $ABO_3$. The stoichiometric ratio of the A-site atom, the B-site atom, and the oxygen atom in the perovskite oxide represented by General Formula $ABO_3$ is 1:1:3.

The piezoelectric film 22 is formed by a sol-gel method. In the sol-gel method, an inorganic oxide is formed by hydrolyzing and polycondensing organic metal compounds, such as metal alkoxide, with a solution system to grow the metal-oxygen-metal bond, and then finally sintering the resultant substance.

In this embodiment, a sol (solution) for forming the piezoelectric film 22 is formed by mixing 2-n-butoxyethanol as a main solvent, for example, with titanium tetraisopropoxide or tetra-n-propoxyzirconium, stirring the mixture at room temperature, adding lead acetate thereto, heating the mixture to 80° C., and then stirring the mixture under heating. Furthermore, the sol is spin-coated, dried at about 180° C., and then degreased at about 400° C. to form a gel film which is a precursor of the piezoelectric film 22. The degreasing is eliminating the organic components of the gel film as $NO_2$, $CO_2$, $H_2O$, and the like, for example. Then, the gel film is heat-treated at a temperature of 600° C. to 800° C., for example, using an RTA (Rapid Thermal Annealing) apparatus or a diffusion furnace for crystallization to thereby form the piezoelectric film 22 (perovskite oxide containing a lead atom, a zirconium atom, and a titanium atom).

The piezoelectric film 22 can also be formed by chemical film formation methods, such as a CVD method, physical film formation methods, such as a sputtering method and an ion plating method, and the like.

The lead atoms contained in the gel film which is a precursor of the piezoelectric film 22 have steam pressure higher than that of the zirconium atom and the titanium atom contained in the gel film, and thus are likely to evaporate. Therefore, when the gel film is heat-treated at a temperature of 600° C. to 800° C., for example, for crystallization, some of the lead atoms evaporate and are not taken into the crystal.

For example, when a gel film in a state where the stoichiometric ratio of the A-site atom, the B-site atom, and the oxygen atom is 1:1:3 (hereinafter referred to as a normal-state gel film) is formed, and then the normal-state gel film is heat-treated for crystallization to form the piezoelectric film 22, the lead atoms evaporate by the heat treatment. Therefore, in the piezoelectric film 22, the stoichiometric ratio of the A-site atom, the B-site atom, and the oxygen atom is not 1:1:3 and the ratio of the A-site atom to the B-site atom is smaller than 1. Therefore, the piezoelectric film 22 formed by heat-treating the normal-state gel film has the A-site (crystal defect) where no lead atom is disposed, and the crystal defect causes an increase in a leakage current and a reduction in a withstand voltage.

For example, when a gel film containing a larger number of lead atoms as compared with the normal-state gel film, and then the gel film is heat-treated for crystallization to form the piezoelectric film 22, the influence of the lead atoms evaporating by the heat treatment is reduced, which reduces the number of the A-sites (crystal defect) where no lead atom is disposed in the piezoelectric film 22. Therefore, in the piezoelectric film 22 formed by heat-treating the gel film containing a larger number of lead atoms as compared with the normal-state gel film, a leakage current decreases and the withstand voltage increases as compared with the piezoelectric film 22 formed by heat-treating the normal-state gel film.

However, when the gel film which is a precursor of the piezoelectric film 22 contains an excessively large number of lead atoms (when lead atoms are excessively contained) as compared with the normal-state gel film, the piezoelectric film 22 formed by heat-treating the gel film excessively containing lead atoms excessively contains lead atoms, and the lead atom is also disposed in the B-site in addition to the A-site, for example. More specifically, the piezoelectric film 22 obtained by heat-treating the gel film excessively containing the lead atoms has a portion where the lead atom is disposed in the B-site in addition to the A-site. The portion where the lead atom is disposed in the B-site in addition to the A-site is a so-called lead oxide and does not have piezoelectric characteristics. Therefore, in the piezoelectric film 22 obtained by heat-treating the gel film excessively containing lead atoms, the piezoelectric characteristics remarkably deteriorate.

Thus, in the piezoelectric film 22 containing the perovskite oxide containing a lead atom, a zirconium atom, and a titanium atom, the film quality changes depending on the states of the lead atoms disposed in the crystal lattice. Therefore, in order to form the piezoelectric film 22 excellent in the film quality, it is important to properly control the states of the lead atoms disposed in the crystal lattice.

However, the piezoelectric film 22 containing the perovskite oxide containing a lead atom, a zirconium atom, and a titanium atom has had a problem that there is no method for properly evaluating the states of the lead atoms disposed in the crystal lattice.

For example, the composition (leaden content) of the piezoelectric film 22 can be evaluated by analysis. However, even when the composition of the piezoelectric film 22 is the same, for example, even when the stoichiometric ratio of the lead atom (A-site atom) and the zirconium atom and the titanium atom (B-site atom) is 1:1, the performance of the piezoelectric film 22 changes when the states of the lead atoms disposed in the A-site are different depending on the formation conditions (sol formation conditions, gel film formation conditions, gel film firing conditions, and the like) of the piezoelectric film 22.

Therefore, it is required to evaluate the states of the lead atoms in the piezoelectric film 22 in terms of the crystal level. Furthermore, when the evaluation of the states of the lead atoms in terms of the crystal level can be achieved, the evaluation method can contribute to an improvement of the film quality, the optimization of the film quality thereof, and the like of the piezoelectric film 22.

Evaluation of Lead Atom in Piezoelectric Film

The present inventors have found the fact that the states of the lead atoms in the piezoelectric film 22 can be evaluated in terms of the crystal level, when focusing on a specific peak of a radial distribution function obtained by Fourier-transforming an extended X-ray absorption fine structure (EXAFS) spectrum at the L3 absorption edge of the lead atom in the radial distribution function, and therefore, the details are described below.

An X-ray absorption fine structure (XAFS) is a fine structure (vibration structure) of the absorption coefficients observed from the absorption edge to the 1000 eV energy region among the absorption spectra obtained by irradiating a substance with X-rays. A fine structure of an absorption coefficient observed in the 50 to 1000 eV region in the energy region is the extended X-ray absorption fine structure (EXAFS). Furthermore, the types of an atom adjacent to a certain atom and an atom adjacent to the adjacent atom can be specified by analyzing the EXAFS spectrum, and the interatomic distance of these atoms and the like can be specified. Furthermore, the degree of presence of these atoms can be assumed from the height of the peak of the radial distribution function obtained by Fourier-transforming the EXAFS spectrum.

Figure 4:
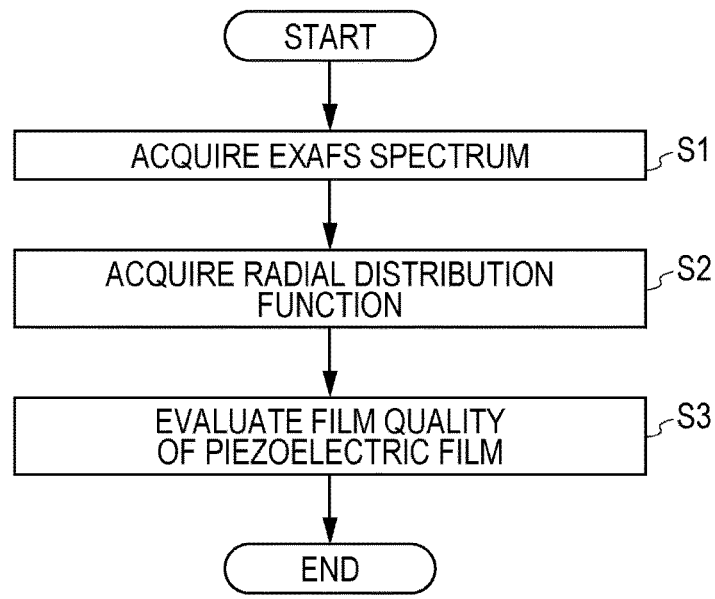
FIG. 4 is a process flow illustrating a method for evaluating a piezoelectric film according to an embodiment.
Figure 5:
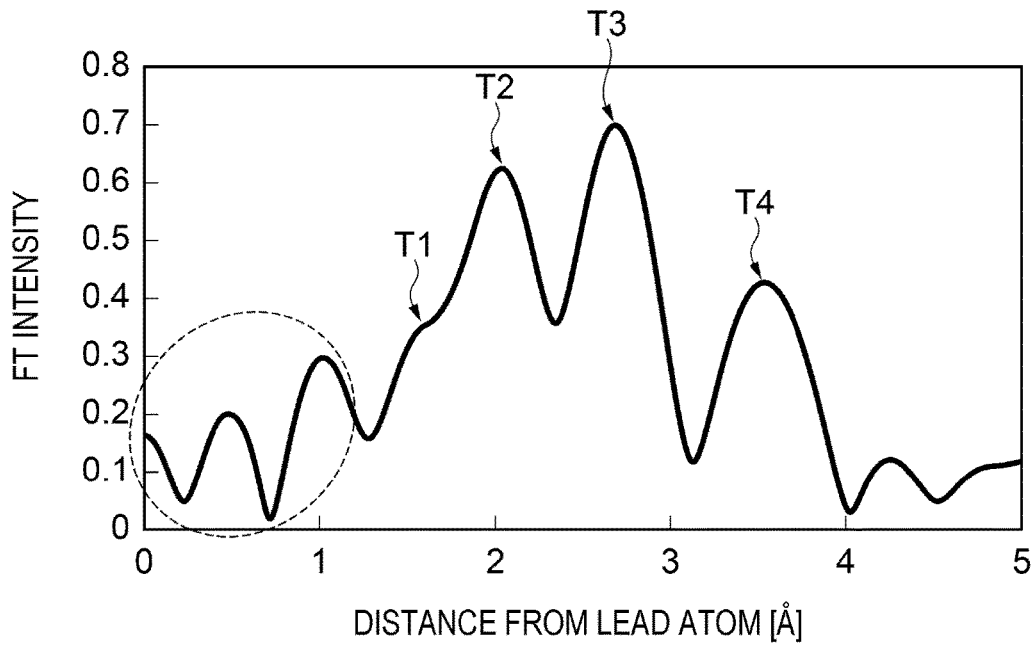
FIG. 5 is a radial distribution function acquired by Fourier-transforming an extended X-ray absorption fine structure (EXAFS) of a spectrum at the L3 absorption edge of a lead atom.

FIG. 4 is a process flow illustrating a method for evaluating the piezoelectric film according to this embodiment. FIG. 5 is the radial distribution function acquired by Fourier-transforming the extended X-ray absorption fine structure (EXAFS) spectrum at the L3 absorption edge of a lead atom. The vertical axis of FIG. 5 represents the vibration intensity (FT intensity) after the Fourier-transformation and the horizontal axis of FIG. 5 represents the distance from a lead atom.

A method for obtaining the radial distribution function is more specifically described. First, a background noise is subtracted from XAFS spectrum data by a common method. Then, a baseline with an intensity axis of 0 in which the average intensity within the range of −150 eV to −30 eV is 0 is set with the absorption edge energy (E0) as the starting point. Moreover, a baseline with an intensity axis of 1 in which the average intensity within the range of +130 eV to +750 eV is 1 is also set. Herein, the two baselines are set so that the absorption edge energy (E0) is positioned at the midpoint of the two baselines on the rise spectrum near the absorption edge energy (E0). Then, the two baselines are replaced by straight lines, and the waveform is adjusted. By this operation, the energy (unit: eV) axis is replaced by a wave number (k, Unit: 1/Å) axis, and a vibration component of the EXAFS is extracted. Next, the spectrum obtained by the operation is multiplied by the cube of k, and then Fourier transformation is carried out. A k region in which the Fourier transformation is carried out is set to 2 to 8.5 (1/Å). Thus, the radial distribution function in which the Y-axis represents the intensity and the X-axis represents the interatomic distance R is obtained.

As illustrated in FIG. 4, the method for evaluating the piezoelectric film according to this embodiment is a method for evaluating the piezoelectric film 22 containing the perovskite oxide containing a lead atom, a zirconium atom, and a titanium atom and includes a process (Step S1) of acquiring the extended X-ray absorption fine structure (EXAFS) spectrum at the L3 absorption edge of the lead atom of the piezoelectric film 22, a process (Step S2) of Fourier-transforming the EXAFS spectrum to acquire a radial distribution function, and a process (Step S3) of evaluating the film quality of the piezoelectric film 22.

In Step S1, the piezoelectric film 22 is irradiated with synchrotron radiation (X-rays) of the Super Photon ring-8 GeV (SPring-8), for example, and then the extended X-ray absorption fine structure (EXAFS) spectrum at the L3 absorption edge of a lead atom is acquired.

In Step S2, a radial distribution function is acquired by Fourier-transforming the EXAFS spectrum at the L3 absorption edge of a lead atom. In order to acquire the radial distribution function, "Athena" which is XAFS analysis software was used.

As illustrated in FIG. 5, the radial distribution function acquired by Fourier-transforming the EXAFS spectrum at the L3 absorption edge of a lead atom has a first peak T1 having a distance from the lead atom of about 1.4 Å, a second peak T2 having a distance from the lead atom of about 2.0 Å, a third peak T3 having a distance from the lead atom of about 2.6 Å, and a fourth peak T4 having a distance from the lead atom of about 3.5 Å.

In the following description, the distance from the lead atom in the first peak T1 is referred to as a first distance R1, the distance from the lead atom in the second peak T2 is referred to as a second distance R2, the distance from the lead atom in the third peak T3 is referred to as a third distance R3, and the distance from the lead atom in the fourth peak T4 is referred to as a fourth distance R4. More specifically, the first distance R1 shows the position of the first peak T1, the second distance R2 shows the position of the second peak T2, the third distance R3 shows the position of the third peak T3, and the fourth distance R4 shows the position of the fourth peak T4.

The radial distribution function acquired by Fourier-transforming the EXAFS spectrum at the L3 absorption edge of the lead atom has the peaks in a region surrounded by the dashed line, i.e., in a region where the distance from the lead atom is 1 Å or less. The peaks in the region where the distance from the lead atom is 1 Å or less (peaks in the region surrounded by the dashed line) are ghost peaks which have no physical meaning and are generated in the process of Fourier-transforming the EXAFS spectrum.

According to the detailed examination of the present inventors, the first distance R1, the second distance R2, the third distance R3, and the fourth distance R4 change depending on the formation conditions (gel film composition, heat treatment conditions of the gel film, and the like) of the piezoelectric film 22. When the formation conditions of the piezoelectric film 22 are changed, the first distance R1 of the first peak T1 is in the range of 1.2 Å to 1.6 Å (1.4±0.2 Å), the second distance R2 of the second peak T2 is in the range of 1.8 Å to 2.2 Å (2.0±0.2 Å), the third distance R3 of the third peak T3 is in the range of 2.4 Å to 2.8 Å (2.6±0.2 Å), and the fourth distance R4 of the fourth peak T4 is in the range of 3.3 Å to 3.7 Å (3.5±0.2 Å).

The maximum values of the FT intensities at the peaks T1, T2, and T3 are the intensities of the peaks T1, T2, and T3 and show the degree of presence of atoms in the distances R1, R2, and R3 from the lead atom. For example, when the intensity of the first peak T1 is high, a larger number of atoms are present in the first distance R1 as compared with the case where the intensity P1 of the first peak is low. When the intensity P2 of the second peak is high, a larger number of atoms are present in the second distance R2 as compared with the case where the intensity P2 of the second peak is low. When the intensity P3 of the third peak is high, a larger number of atoms are present in the third distance R3 as compared with the case where the intensity P3 of the third peak is low.

In the following description, the intensity of the first peak T1 is referred to as an intensity P1 of the first peak, the intensity of the second peak T2 is referred to as an intensity P2 of the second peak, and the intensity of the third peak T3 is referred to as an intensity P3 of the third peak.

As a result of comparing with the EXAFS theoretical calculation, the second peak T2 was a peak due to the oxygen atom disposed closest to the lead atom (hereinafter referred to as closest oxygen atom). Furthermore, it was also confirmed by the simulation evaluation about the perovskite oxide (perfect crystal free from crystal defects) in which the stoichiometric ratio of the A-site atom, the B-site atom, and the oxygen atom is 1:1:3 that the second distance R2 is the distance between the lead atom and the closest oxygen atom.

Therefore, the second peak T2 is a peak due to the closest oxygen atom in the perfect crystal free from crystal defects. In other words, the second peak T2 is a peak due to the closest oxygen atom in a portion where the crystal is not distorted by crystal defects, impurities, or the like.

When the piezoelectric film 22 is formed by changing the lead content in the gel film which is a precursor of the piezoelectric film 22 and the state of the lead atom disposed in the crystal of the piezoelectric film 22 is changed by changing the amount of the lead atom to be taken in of the piezoelectric film 22, the intensity P1 of the first peak greatly changes and the changes in the intensity P2 of the second peak and the intensity P3 of the third peak are small.

For example, when the formation conditions of the piezoelectric film 22 were changed in a direction where the A-site (crystal defect), where no lead atom is disposed, increases, the intensity P1 of the first peak increased. For example, when the formation conditions of the piezoelectric film 22 were changed in a direction where the A-site (crystal defect), where no lead atom is disposed, decreases, the intensity P1 of the first peak decreased. In any condition, the changes in the intensity P2 of the second peak and the intensity P3 of the third peak were small.

Therefore, it is considered that the first peak T1 is a peak due to the closest oxygen atom in a portion where the crystal is distorted by lattice defects or impurities.

The third peak T3 was a peak due to the oxygen atom disposed second closest to the lead atom after the closest oxygen atom (hereinafter referred to as second closest oxygen atom) as a result of comparing with the EXAFS theoretical calculation. Furthermore, it was also confirmed by the simulation evaluation about the perovskite oxide (perfect crystal without crystal defects) in which the stoichiometric ratio of the A-site atom, the B-site atom, and the oxygen atom is 1:1:3 that the third distance R3 is the distance between the lead atom and the second closest oxygen atom.

Therefore, the third peak T3 is a peak due to the second closest oxygen atom in a portion where the crystal is not distorted by crystal defects, impurities, or the like.

The fourth peak T4 was a peak due to the B-site atom (zirconium atom, titanium atom) or a peak due to the oxygen atom disposed farther than the second closest oxygen atom relative to the lead atom as a result of comparing with the EXAFS theoretical calculation.

As described above, when the formation conditions of the piezoelectric film 22 are changed in a direction where the A-site (crystal defects), where no lead atom is disposed, increases, the intensity P1 of the first peak increases and, when the formation conditions of the piezoelectric film 22 are changed in a direction where the A-site (crystal defects), where no lead atom is disposed, decreases, the intensity P1 of the first peak decreases. Therefore it can be evaluated by observing the intensity P1 of the first peak that the number of the A-sites (crystal defects), where no lead atom is disposed, is large or the number of the A-sites (crystal defects), where no lead atom is disposed, is small.

Therefore, the observation of the intensity P1 of the first peak enables the evaluation of the state of the lead atom in terms of the crystal level.

In Step S3, the film quality of the piezoelectric films 22 is evaluated and a preferable piezoelectric film 22 is determined from the relationship between the specific peaks (first peak T1, second peak T2, third peak T3) in the radial distribution function acquired by Fourier-transforming the EXAFS spectrum at the L3 absorption edge of the lead atom and the performance of the piezoelectric elements 20.

In Step S3, the level (High or Low) of the intensity P1 of the first peak is evaluated by only the intensity P1 of the first peak and the level (High or Low) of the intensity P1 of the first peak is evaluated by the relative value (P1/P2) of the intensity P1 of the first peak based on the intensity P2 of the second peak and the relative value (P1/P3) of the intensity P1 of the first peak based on the intensity P3 of the third peak evaluate. More specifically, in Step S3, the level (High or Low) of the intensity P1 of a first peak is evaluated by the relative value (P1/P2) obtained by dividing the intensity P1 of the first peak by the intensity P2 of the second peak or the relative value (P1/P3) obtained by dividing the intensity P1 of the first peak by the intensity P3 of the third peak.

The relative value (P1/P2) of the intensity P1 of the first peak based on the intensity P2 of the second peak is an example of the "value obtained by dividing the intensity of the first peak by the intensity of the second peak". The relative value (P1/P3) of the intensity P1 of the first peak based on the intensity P3 of the third peak is an example of the "value obtained by dividing the intensity of the first peak by the intensity of the third peak".

The intensity P1 of the first peak is likely to change and tends to include abnormal points due to a disturbance.

Therefore, it is preferable to evaluate the level (High or Low) of the intensity P1 of the first peak by the relative value to the reference values (intensity P2 of the second peak, intensity P3 of the third peak) which are less likely to change.

Furthermore, a case where the intensity P2 of the second peak and the intensity P3 of the third peak also include abnormal points due to a disturbance is assumed. Therefore, it is preferable to evaluate the level (High or Low) of the intensity P1 of the first peak by at least one of the relative value (P1/P2) of the intensity P1 of the first peak based on the intensity P2 of the second peak and the relative value (P1/P3) of the intensity P1 of the first peak based on the intensity P3 of the third peak.

Figure 6:
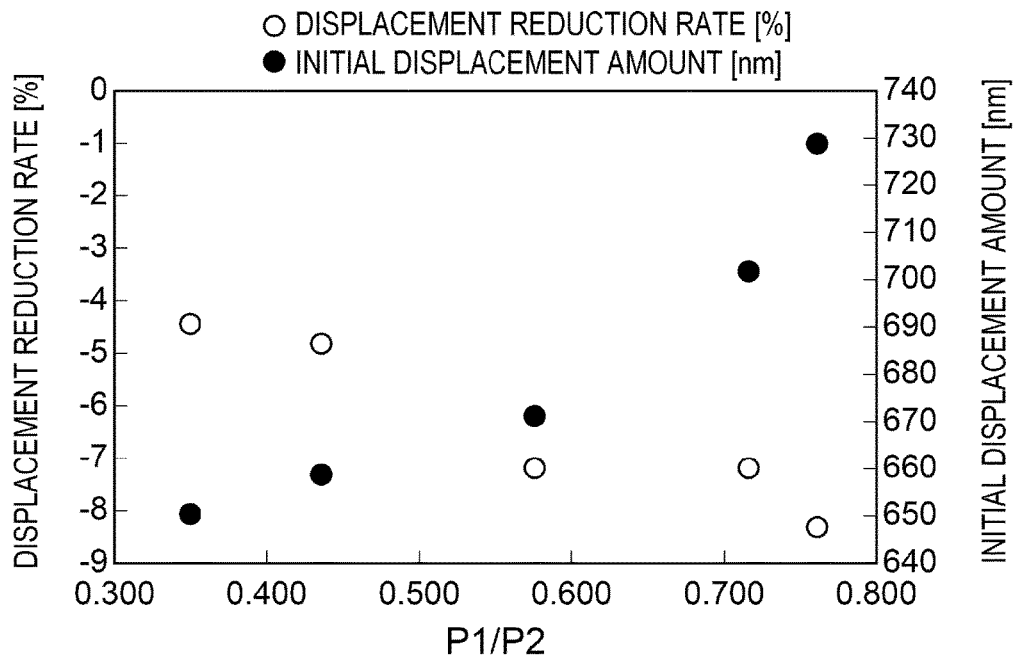
FIG. 6 is a graph illustrating the relationship between a relative value (P1/P2) of the intensity of a first peak based on the intensity of a second peak and the initial displacement amount and the displacement reduction rate.
Figure 7:
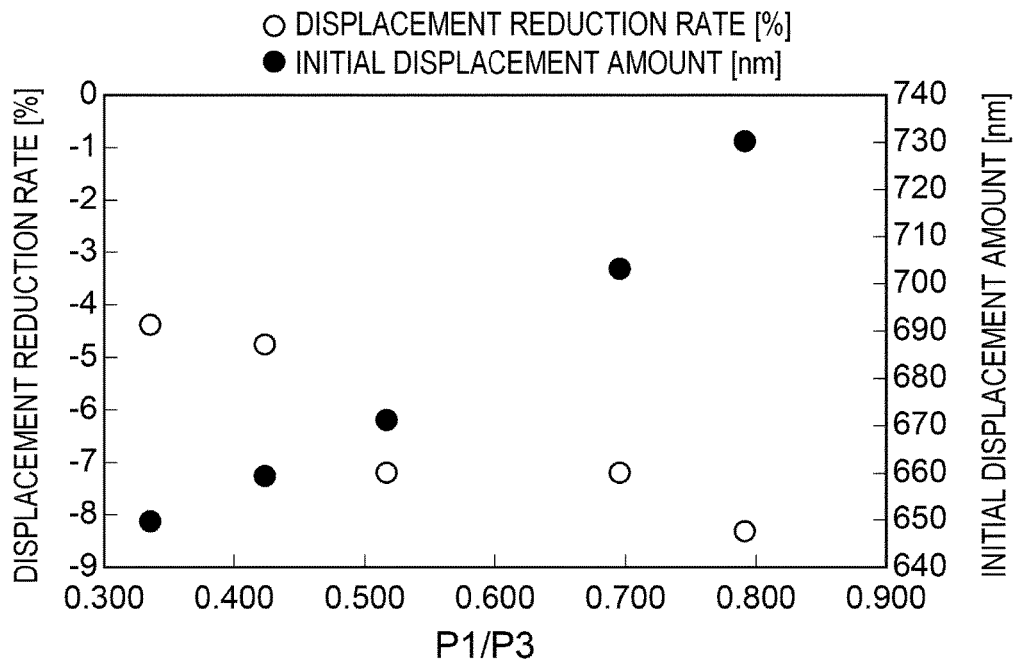
FIG. 7 is a graph illustrating the relationship between a relative value (P1/P3) of the intensity of the first peak based on the intensity of a third peak and the initial displacement amount and the displacement reduction rate.

FIG. 6 is a graph showing the relationship between the relative value (P1/P2) of the intensity of the first peak based on the intensity of the second peak and the initial displacement amount and the displacement reduction rate. FIG. 7 is a graph showing the relationship between the relative value (P1/P3) of the intensity of the first peak based on the intensity of the third peak and the initial displacement amount and the displacement reduction rate.

The initial displacement amount is the displacement amount of the piezoelectric elements 20 at the early stage of the driving after performing polling processing (45 V, 20 minutes) to the liquid ejecting head 1. The displacement reduction rate is the reduction rate of the displacement amount of the piezoelectric elements 20 after performing polling processing (45 V, 20 minutes) to the liquid ejecting head 1, and then performing pulse drive (5 pl) 19 billion times.

In the piezoelectric film 22, the displacement amount decreases due to a so-called fatigue phenomenon in which the polarization direction is partially fixed so as to be in parallel with the electric field application direction with the progress of time due to the repetition of rotary expansion and contraction of the polarization during the driving. Therefore, the displacement amount of the piezoelectric elements 20 after performing the pulse drive 19 billion times (hereinafter referred to as displacement amount after the repeated driving) is smaller than the displacement amount of the piezoelectric elements 20 at the early stage of the driving (the initial displacement amount). In FIG. 6 and FIG. 7, the displacement reduction rate is calculated by dividing a difference between the displacement amount after the repeated driving and the initial displacement amount by the initial displacement amount.

In FIG. 6, the P1/P2 is the relative value of the intensity P1 of the first peak based on the intensity P2 of the second peak. Therefore, in a state where the P1/P2 is large, the piezoelectric film 22 is in a state where the number of crystal defects is large and the distortion of the crystal is large. Furthermore, in a state where the P1/P2 is small, the piezoelectric film 22 is in a state where the number of crystal defects is small and the distortion of the crystal is small.

In FIG. 7, the P1/P3 is the relative value of the intensity P1 of the first peak based on the intensity P3 of the third peak. Therefore, in a state where the P1/P3 is large, the piezoelectric film 22 is in a state where the number of crystal defects is large and the distortion of the crystal is large. Furthermore, in a state where the P1/P3 is small, the piezoelectric film 22 is in a state where the number of crystal defects is small and the distortion of the crystal is small.

As illustrated in FIG. 6, when the P1/P2 increases from 0.35 to 0.76, the initial displacement amount increases from 650 nm to 730 nm, the displacement reduction rate decreases from −4.4% to −8.3%, and the absolute value of the displacement reduction rate increases.

When the P1/P2 is small, the initial displacement amount of the piezoelectric elements 20 is small as compared with a case where the P1/P2 is large but the displacement amount of the piezoelectric elements 20 is less likely to change by the repeated driving. When the P1/P2 is large, the initial displacement amount of the piezoelectric elements 20 is large as compared with the case where the P1/P2 is small but the displacement amount of the piezoelectric elements 20 is likely to change by the repeated driving. More specifically, the securing of the initial displacement amount and the control of the displacement reduction rate have a trade-off relationship.

As illustrated in FIG. 7, when the P1/P3 increases from 0.35 to 0.79, the initial displacement amount increases from 650 nm to 730 nm and the displacement reduction rate decreases from −4.4% to −8.3%.

When the P1/P3 is small, the initial displacement amount of the piezoelectric elements 20 is small as compared with a case where the P1/P3 is large but the displacement amount of the piezoelectric elements 20 is less likely to change by the repeated driving. When the P1/P3 is large, the initial displacement amount of the piezoelectric elements 20 is large as compared with the case where the P1/P3 is small but the displacement amount of the piezoelectric elements 20 is likely to change by the repeated driving. More specifically, the securing of the initial displacement amount and the control of the displacement reduction rate have a trade-off relationship.

When the repeated driving is performed, the displacement amount of the piezoelectric elements 20 decreases due to the fatigue phenomenon of the piezoelectric film 22, and therefore the displacement reduction rate is preferably lower.

In the liquid ejecting apparatus 100, when the displacement reduction rate exceeds 8%, an image quality reduction of an NG level is caused, and therefore the displacement reduction rate is preferably 8% or less. More specifically, in order for the liquid ejecting apparatus 100 to provide an image of an image quality which can be practically used even when used over a long period of time, the displacement reduction rate is preferably 8% or less.

Furthermore, in order for the liquid ejecting apparatus 100 to provide an image of an excellent image quality in which a degradation of the image quality is prevented even when used over a long period of time, the displacement reduction rate is preferably 5% or less.

Therefore, the displacement reduction rate is preferably 8% or less and more preferably 5% or less.

For example, when the density of the nozzle openings 71 (piezoelectric elements 20) is increased and a region where the piezoelectric film 22 can be deformed is narrowed in the liquid ejecting head 1, the piezoelectric film 22 is difficult to be deformed and the ink exclusion volume in the pressure generating chambers 12 decreases, and therefore the initial displacement amount is preferably larger. Even when the density of the nozzle openings 71 (piezoelectric elements 20) is increased, the initial displacement amount is preferably 600 nm or more in order to secure a predetermined ink exclusion volume.

From FIG. 6 and FIG. 7, when the P1/P2 is 0.75 or less or when the P1/P3 is 0.75 or less, the conditions where the displacement reduction rate is 8% or less and the initial displacement amount is 600 nm or more are satisfied. Therefore, the piezoelectric film 22 in which the P1/P2 is 0.75 or less or the P1/P3 is 0.75 or less is preferable.

From FIG. 6 and FIG. 7, when the P1/P2 is 0.43 or less or when the P1/P3 is 0.43 or less, the conditions where the displacement reduction rate is 5% or less and the initial displacement amount is 600 nm or more are satisfied. Therefore, the piezoelectric film 22 in which the P1/P2 is 0.43 or less or in which the P1/P3 is 0.43 or less is more preferable.

Furthermore, when the P1/P2 and the P1/P3 are smaller than 0.35, the piezoelectric film 22 excessively contain lead atoms, which sometimes causes segregation of lead oxides (portion not having piezoelectric characteristics) in the piezoelectric film 22. When the P1/P2 and P1/P3 are smaller than 0.35, lead oxides (portion not having piezoelectric characteristics) are not always segregated in the piezoelectric film 22 but lead oxides (portion not having piezoelectric characteristics) are sometimes segregated in the piezoelectric film 22 by the fluctuation of the formation conditions of the piezoelectric film 22.

On the other hand, when the P1/P2 and the P1/P3 are 0.35 or more, lead oxides (portion not having piezoelectric characteristics) are not segregated in the piezoelectric film 22 by the fluctuation of the formation conditions of the piezoelectric film 22. Therefore, in order to prevent the segregation of lead oxides (portion not having piezoelectric characteristics) in the piezoelectric film 22 due to the fact that the piezoelectric film 22 excessively contains lead atoms, the P1/P2 is preferably 0.35 or more and the P1/P3 is preferably 0.35 or more.

Based on the analysis results described above, it is judged in Step S3 that, in the piezoelectric film 22 in which the P1/P2 is 0.35 or more and 0.75 or less or in the piezoelectric film 22 in which the P1/P3 is 0.35 or more and 0.75 or less, the piezoelectric element 20 satisfies both the securing of the initial displacement amount and the control of the displacement reduction rate and the piezoelectric films 22 have preferably film quality.

A case where the intensity P2 of the second peak and the intensity P3 of the third peak serving as the standard for evaluating the level (High or Low) of the intensity P1 of the first peak have abnormal values by a disturbance is assumed, and therefore it is judged in Step S3 that the piezoelectric film 22 in which both the P1/P2 and the P1/P3 are 0.35 or more and 0.75 or less and the piezoelectric film 22 in which either the P1/P2 or the P1/P3 is 0.35 or more and 0.75 or less have preferable film quality.

Furthermore, it is judged in Step S3 that, when both the P1/P2 and the P1/P3 are 0.35 or more and 0.43 or less and when either the P1/P2 or the P1/P3 is 0.35 or more and 0.43 or less, the displacement reduction rate is controlled to a more preferable state, and therefore the piezoelectric film 22 in which both the P1/P2 and the P1/P3 are 0.35 or more and 0.43 or less and the piezoelectric film 22 in which either the P1/P2 or the P1/P3 is 0.35 or more and 0.43 or less have more preferable film quality.

Thus, it is preferable that the radial distribution function obtained by Fourier-transforming the extended X-ray absorption fine structure (EXAFS) spectrum at the L3 absorption edge of the lead atom of the piezoelectric film 22 has the first peak T1 having the distance R1 from the lead atom of 1.4±0.2 Å, the second peak T2 having the distance R2 from the lead atom of 2.0±0.2 Å, and the third peak T3 having the distance R3 from the lead atom of 2.6±0.2 Å and the piezoelectric film 22 satisfies at least either one of the conditions that the relative value (P1/P2) obtained by dividing the intensity P1 of the first peak by the intensity P2 of the second peak is in the range of 0.35 to 0.75 and the relative value (P1/P3) obtained by dividing the intensity P1 of the first peak by the intensity P3 of the third peak is in the range of 0.35 to 0.75.

Furthermore, it is more preferable that the radial distribution function obtained by Fourier-transforming the extended X-ray absorption fine structure (EXAFS) spectrum at the L3 absorption edge of the lead atom of the piezoelectric film 22 has the first peak T1 having the distance R1 from the lead atom of 1.4±0.2 Å, the second peak T2 having the distance R2 from the lead atom of 2.0±0.2 Å, and the third peak T3 having the distance R3 from the lead atom of 2.6±0.2 Å and the piezoelectric film 22 satisfies at least either one of the conditions that the relative value (P1/P2) obtained by dividing the intensity P1 of the first peak by the intensity P2 of the second peak is in the range of 0.35 to 0.43 and the relative value (P1/P3) obtained by dividing the intensity P1 of the first peak by the intensity P3 of the third peak being in the range of 0.35 to 0.43.

The method for evaluating the piezoelectric film according to this embodiment is applicable to all oxides having the perovskite structure represented by General Formula $ABO_3$.

For example, the method for evaluating the piezoelectric film according to this embodiment is also applicable to, in addition to the lead zirconate titanate (PZT) described above, lead titanate ($PbTiO_3$), lead zirconate ($PbZrO_3$), lead zirconate titanate niobate ($Pb(Zr, Ti, Nb)O_3$), lead lanthanum titanate ($(Pb, La), TiO_3$), lead lanthanum zirconate titanate (Pb, La) (Zr, Ti) ($O_3$), lead zirconium titanate magnesium niobate ($Pb(Zr, Ti) (Mg, Nb)O_3$), and the like.

For example, the method for evaluating the piezoelectric film described above is also applicable to lead-free piezoelectric materials containing no lead, specifically, oxides having the perovskite structure containing bismuth ferrite, manganese ferrite bismuth, barium titanate, bismuth potassium titanate, and the like.

By applying the method for evaluating the piezoelectric film according to this embodiment to all oxides having the perovskite structure represented by General Formula $ABO_3$, the film quality of the oxides having the perovskite structure represented by General Formula $ABO_3$ can be optimized. Furthermore, the conditions (P1/P2, P1/P3) of the oxides having the perovskite structure optimized by the method for evaluating the piezoelectric film according to this embodiment are also included in the technical scope of this application.

The entire disclosure of Japanese Patent Application No. 2016-226672, filed Nov. 22, 2016, is expressly incorporated by reference herein.

What is claimed is:

1. A method for evaluating a piezoelectric film containing a perovskite oxide containing a lead atom, a zirconium atom, and a titanium atom, the method comprising:
    irradiating the piezoelectric film with X-rays to acquire an extended X-ray absorption fine structure (EXAFS) spectrum at an L3 absorption edge of the lead atom;
    Fourier-transforming the extended X-ray absorption fine structure (EXAFS) spectrum to acquire a radial distribution function; and
    acquiring intensity of a first peak having a distance from the lead atom of 1.4±0.2 Å, intensity of a second peak having a distance from the lead atom of 2.0±0.2 Å, and intensity of a third peak having a distance from the lead atom of 2.6±0.2 Å from the radial distribution function, and then evaluating film quality of the piezoelectric film from a value obtained by dividing the intensity of the first peak by the intensity of the second peak and a value obtained by dividing the intensity of the first peak by the intensity of the third peak.

2. A piezoelectric element having a piezoelectric film containing a perovskite oxide containing a lead atom, a zirconium atom, and a titanium atom, wherein
    a radial distribution function obtained by Fourier-transforming an extended X-ray absorption fine structure (EXAFS) spectrum at an L3 absorption edge of the lead atom of the piezoelectric film has a first peak having a distance from the lead atom of 1.4±0.2 Å, a second peak having a distance from the lead atom of 2.0±0.2 Å, and a third peak having a distance from the lead atom of 2.6±0.2 Å, and
    when a value obtained by dividing intensity of the first peak by intensity of the second peak is defined as A and a value obtained by dividing the intensity of the first peak by intensity of the third peak is defined as B,
    the piezoelectric film satisfies at least one of conditions that the A is in a range of 0.35 to 0.75 and the B is in a range of 0.35 to 0.75.

3. A liquid ejecting head comprising a nozzle opening, a pressure generating chamber brought into communication with the nozzle opening, and a piezoelectric element and ejecting liquid from the nozzle opening by an operation of the piezoelectric element, wherein
    the piezoelectric element has a piezoelectric film containing a perovskite oxide containing a lead atom, a zirconium atom, and a titanium atom,
    a radial distribution function obtained by Fourier-transforming an extended X-ray absorption fine structure (EXAFS) spectrum at an L3 absorption edge of the lead atom of the piezoelectric film has a first peak having a distance from the lead atom of 1.4±0.2 Å, a second peak having a distance from the lead atom of 2.0±0.2 Å, and a third peak having a distance from the lead atom of 2.6±0.2 Å, and
    when a value obtained by dividing the intensity of the first peak by intensity of the second peak is defined as A and a value obtained by dividing the intensity of the first peak by intensity of the third peak is defined as B,
    the piezoelectric film satisfies at least one of conditions that the A is in a range of 0.35 to 0.75 and the B is in a range of 0.35 to 0.75.

4. A liquid ejecting apparatus comprising:
the liquid ejecting head according to claim 3.

* * * * *